US011925732B2

(12) United States Patent
Layer et al.

(10) Patent No.: US 11,925,732 B2
(45) Date of Patent: Mar. 12, 2024

(54) DEVICE FOR VOLATILIZING COMPOUNDS WITH A SELECTIVELY ADJUSTABLE HEAT SOURCE

(71) Applicant: The Yankee Candle Company, Inc., South Deerfield, MA (US)

(72) Inventors: James A. Layer, Amherst, MA (US); Robert E. Shave, South Deerfield, MA (US)

(73) Assignee: The Yankee Candle Company, Inc., South Deerfield, MA (US)

( * ) Notice: Subject to any disclaimer, the term of this patent is extended or adjusted under 35 U.S.C. 154(b) by 1050 days.

(21) Appl. No.: 16/509,687

(22) Filed: Jul. 12, 2019

(65) Prior Publication Data

US 2020/0093950 A1 Mar. 26, 2020

Related U.S. Application Data

(60) Provisional application No. 62/736,732, filed on Sep. 26, 2018.

(51) Int. Cl.
*A61L 9/03* (2006.01)
*A01M 1/20* (2006.01)
*A01M 13/00* (2006.01)
*A61L 9/01* (2006.01)

(52) U.S. Cl.
CPC ........... *A61L 9/037* (2013.01); *A01M 1/2077* (2013.01); *A61L 2209/13* (2013.01); *A61L 2209/15* (2013.01)

(58) Field of Classification Search
CPC .............................. A61L 9/037; A01M 1/2077
See application file for complete search history.

(56) References Cited

U.S. PATENT DOCUMENTS

| 4,968,487 A | * | 11/1990 | Yamamoto | A01M 1/2077 210/507 |
| 5,038,394 A | * | 8/1991 | Hasegawa | A01M 1/2077 392/395 |
| 5,222,186 A | * | 6/1993 | Schimanski | A61L 9/03 392/405 |
| 5,290,546 A | * | 3/1994 | Hasegawa | A01M 1/2077 514/765 |

(Continued)

*Primary Examiner* — Helena Kosanovic
*Assistant Examiner* — Lawrence H Samuels
(74) *Attorney, Agent, or Firm* — Husch B (57) ABSTRACT

A device for variable volatilization of a compound includes first and second heating elements that cooperate to form a heating chamber and each having a movement enabling structure; the movement enabling structures being configured to allow movement of the first and second heating elements relative to one another; an adjustment mechanism cooperating with the movement enabling structures to produce selective relative movement of the first and second heating elements; and wherein movement of the adjustment mechanism in a first direction results in relative movement of the heating elements away from one another and movement in a second direction produces relative movement of the heating elements toward one another resulting in adjustment of the amount of heat within the heating chamber. Methods of adjusting the amount of heat within a heating chamber are also disclosed.

20 Claims, 5 Drawing Sheets

(56) References Cited

U.S. PATENT DOCUMENTS

| | | | | |
|---|---|---|---|---|
| 5,528,020 A * | 6/1996 | Dickens | ............... | H05B 6/362 |
| | | | | 219/637 |
| 5,909,845 A * | 6/1999 | Greatbatch | ......... | A01M 1/2044 |
| | | | | 239/44 |
| 6,285,830 B1 * | 9/2001 | Basaganas Millan | ...................... | |
| | | | | A01M 1/2077 |
| | | | | 261/DIG. 65 |
| 6,466,739 B2 * | 10/2002 | Ambrosi | ................ | A61L 9/037 |
| | | | | 392/395 |
| 6,580,875 B2 * | 6/2003 | Rymer | ................ | A01M 1/2077 |
| | | | | 392/395 |
| 6,735,983 B1 * | 5/2004 | Taru | ................... | C03B 37/0253 |
| | | | | 65/435 |
| 6,827,286 B2 * | 12/2004 | Zobele | ..................... | A61L 9/02 |
| | | | | 122/366 |
| 6,850,697 B2 * | 2/2005 | Basaganas Millan | .. | A61L 9/037 |
| | | | | 392/390 |
| 6,859,615 B2 * | 2/2005 | Yip | ........................ | A61L 9/037 |
| | | | | 392/390 |
| 6,931,202 B2 * | 8/2005 | Pedrotti | .............. | A01M 1/2077 |
| | | | | 392/395 |
| 6,996,335 B2 * | 2/2006 | Zobele | ................ | A01M 1/2077 |
| | | | | 392/386 |
| 7,082,259 B2 * | 7/2006 | Zobele | ................... | A61L 9/037 |
| | | | | 392/390 |
| 7,085,481 B2 * | 8/2006 | Hooks | ................ | A01M 1/2077 |
| | | | | 392/386 |
| 9,669,126 B2 * | 6/2017 | Jaworski | ................. | A61L 9/037 |
| 9,884,133 B2 * | 2/2018 | Tebé Poves | .............. | A61L 2/03 |
| 10,764,963 B2 * | 9/2020 | Davis | ....................... | A61L 9/037 |
| 2002/0159916 A1 * | 10/2002 | Whitby | ................... | A61L 9/035 |
| | | | | 422/4 |
| 2002/0181946 A1 * | 12/2002 | Brown | ............... | A01M 1/2077 |
| | | | | 392/390 |
| 2003/0007787 A1 * | 1/2003 | Rymer | .................... | A61L 9/037 |
| | | | | 392/395 |
| 2003/0095895 A1 * | 5/2003 | O'Loughlin | .............. | A61L 9/03 |
| | | | | 422/306 |
| 2003/0231876 A1 * | 12/2003 | Basaganas Millan | ...................... | |
| | | | | A01M 1/2077 |
| | | | | 392/394 |
| 2004/0021001 A1 * | 2/2004 | Zobele | ..................... | A61L 9/02 |
| | | | | 239/44 |
| 2005/0196159 A1 * | 9/2005 | Zobele | .................... | A61L 9/037 |
| | | | | 392/390 |
| 2005/0276583 A1 * | 12/2005 | Hooks | ................. | A01M 1/2077 |
| | | | | 392/395 |
| 2013/0266297 A1 * | 10/2013 | Ihle | ......... | H05B 3/14 |
| | | | | 219/520 |
| 2014/0037273 A1 * | 2/2014 | Jaworski | ................. | A61L 9/037 |
| | | | | 392/390 |
| 2014/0064714 A1 * | 3/2014 | Ques Ramos | .......... | A61L 9/037 |
| | | | | 392/390 |
| 2016/0345632 A1 * | 12/2016 | Lipowicz | ................ | A24F 40/44 |
| 2018/0103507 A1 * | 4/2018 | Davis | ..................... | A61L 9/037 |

\* cited by examiner

DEVICE FOR VOLATILIZING COMPOUNDS WITH A SELECTIVELY ADJUSTABLE HEAT SOURCE

CROSS REFERENCE TO RELATED APPLICATIONS

This application claims the benefit of U.S. Provisional Application No. 62/736,732, filed Sep. 26, 2018, which is hereby incorporated by reference in its entirety.

FIELD OF INVENTION

The present disclosure relates generally to the field of volatilizing compounds for localized dispersion into the atmosphere and, more particularly, to a device for providing adjustable heat to conduct such volatilization.

BACKGROUND OF THE INVENTION

This section provides background information related to the present disclosure which is not necessarily prior art.

Plug-in scent dispensers are widely marketed and sold. These dispensers use an electrical current, generally provided by a standard wall outlet, to operate heating elements. The heating elements deliver heat to a wick that is saturated with a scented oil from a container associated with the wick. The scented oil is dispersed through evaporation resulting from heat delivered to the wick. Similar devices are utilized to disperse other compounds, such as insecticides.

While initial generations of these dispensers provided a relatively steady dispersal of scented oil into the surrounding atmosphere, later generations of dispensers have sought to provide adjustability of the amount of oil that is volatilized and delivered to the environment. The adjustable amount of oil results in an adjustable intensity of the scent or amount of insecticide or other compound that individuals near the dispenser encounter. For example, in environments having more potentially offensive odors, it may be desirable to increase the intensity of the scent. However, this does result in an increase in the rate at which the compound within the container is dispersed, which in turn results in a more frequent required replacement of the oil container and greater expense. Therefore, it is also desirable for the user to be able to decrease the volatilization rate when the dispenser is used in less odiferous environments in order to maximize the lifespan of a container.

As a result, attempts have been made to produce dispensers that allow for adjustment in the volatilization rate of oil in the dispenser. In general, each of these dispensers makes use of the same single heater design of the prior generation fixed rate dispensers. To provide adjustability, these dispensers include mechanisms that seek to shield the wick from the steady state heat source, and allow for adjustment in the positioning of the shield relative to the heat source. Other dispensers have attempted to solve this issue by adjusting the position of the wick relative to the heat source. In each case, these dispensers have a limitation in that the manipulations of the delivery of heat also decrease the uniformity of whatever amount of heat is delivered to the wick, which can result in incomplete volatilization of the oil in the wick rather than a uniform and either a slower or faster volatilization.

SUMMARY

This section provides a general summary of the disclosure, and is not a comprehensive disclosure of its full scope or all of its features.

According to one aspect of the present disclosure, a device for variable volatilization of a compound includes first and second heating elements that cooperate to form a heating chamber with each first and second heating elements having a movement enabling structure; the movement enabling structures being configured to allow movement of the first and second heating elements relative to one another; an adjustment mechanism cooperating with the movement enabling structures to produce selective relative movement of the first and second heating elements; and wherein movement of the adjustment mechanism in a first direction results in relative movement of the heating elements toward one another and movement in a second direction produces relative movement of the heating elements away from one another, resulting in adjustment of the amount of heat within the heating chamber.

According to another aspect of the present disclosure, methods of adjusting the amount of heat within a heating chamber are also disclosed.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts and/or features throughout several views of the drawings.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure.

DETAILED DESCRIPTION OF THE DRAWINGS

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
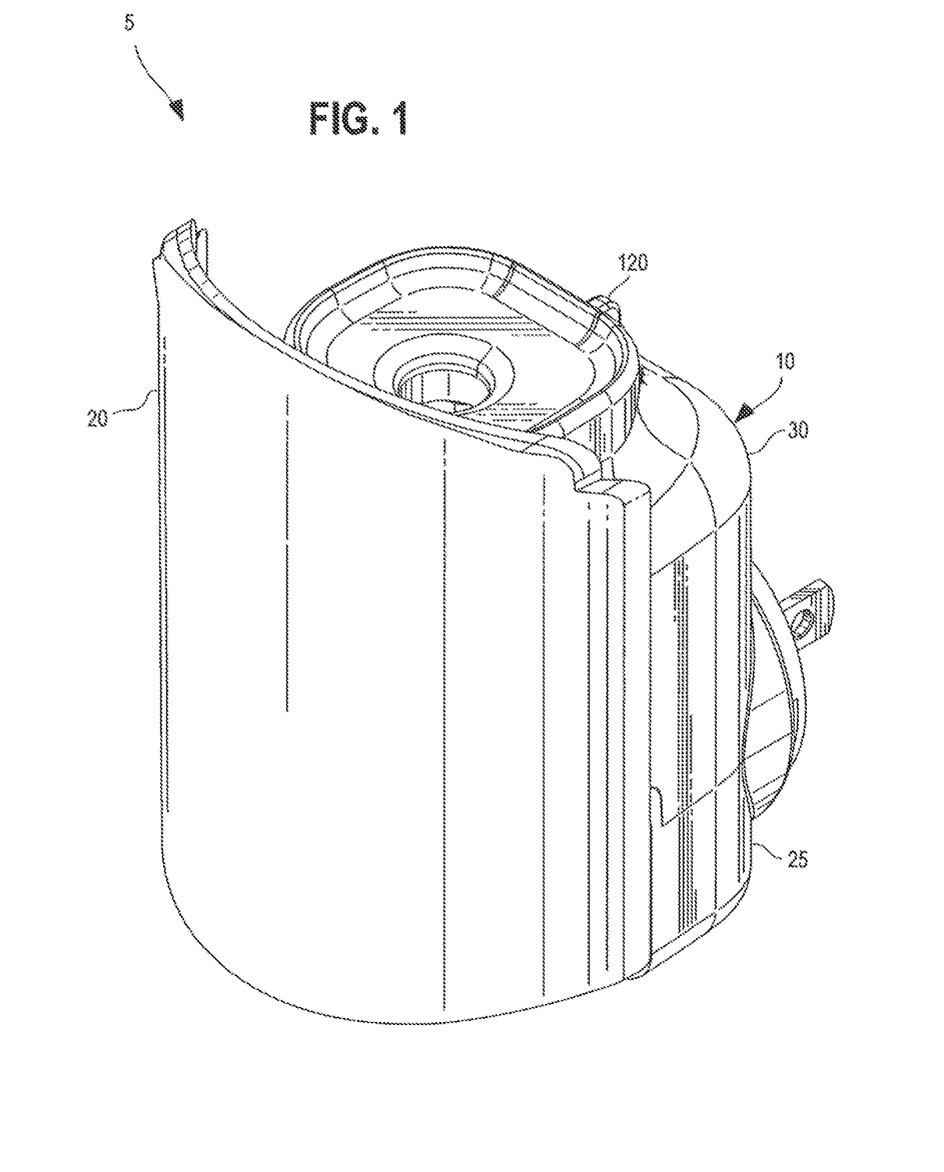
FIG. 1 is a perspective view of a device for volatizing a compound for dispersal to the atmosphere according to one embodiment.

FIGS. 1-5B illustrate various embodiments of a device 5 for the dispersal by volatilization of various compounds, such as fragrances, insecticides, or other materials that may be dispersed into a localized environment by the application of heat via a heating element. As illustrated in FIG. 1, the device 5 includes a housing 10, a bottle 15 (shown in FIG. 2), and a shield 20. The housing 10 includes a lower housing component 25 and an upper housing component 30. The lower housing component 25 and the upper housing component 30 engage each other to form a protective shell surrounding the components of the device 5.

Figure 2:
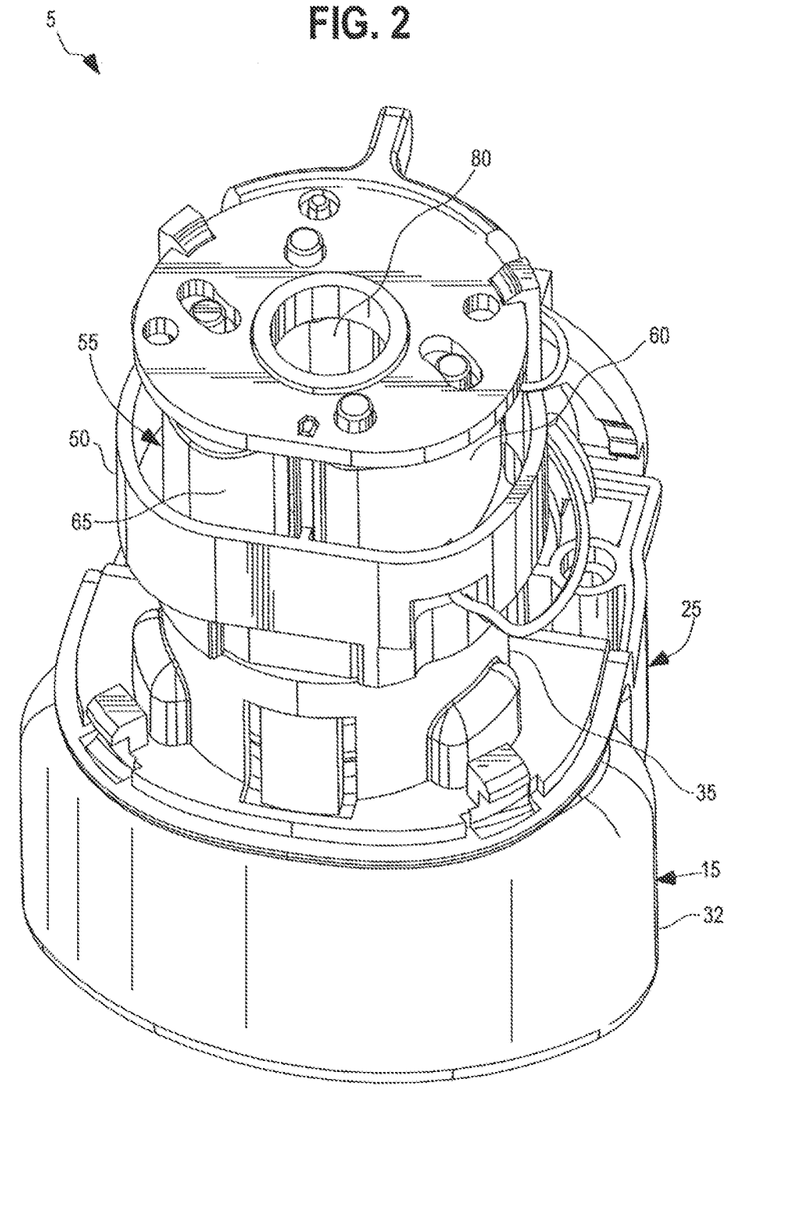
FIG. 2 is a partial perspective view of the device of FIG. 1.

In one embodiment (shown in FIGS. 3 and 4), the bottle 15 may include a generally rectangular storage section 32, and a circular engagement section 33 that extends from the rectangular storage section 32. In other embodiments, however, the bottle 15 may be different shapes and sizes. The bottle 15 further includes a wick 34 that extends from the engagement section 33. The storage section 32 may be located and positioned adjacent to and abut the lower housing component 25 as seen in FIG. 2. The engagement section 33 is selectively engageable with a container receptacle 35 located within the lower housing component 25 as will be described in more detail hereinafter.

Figure 3:
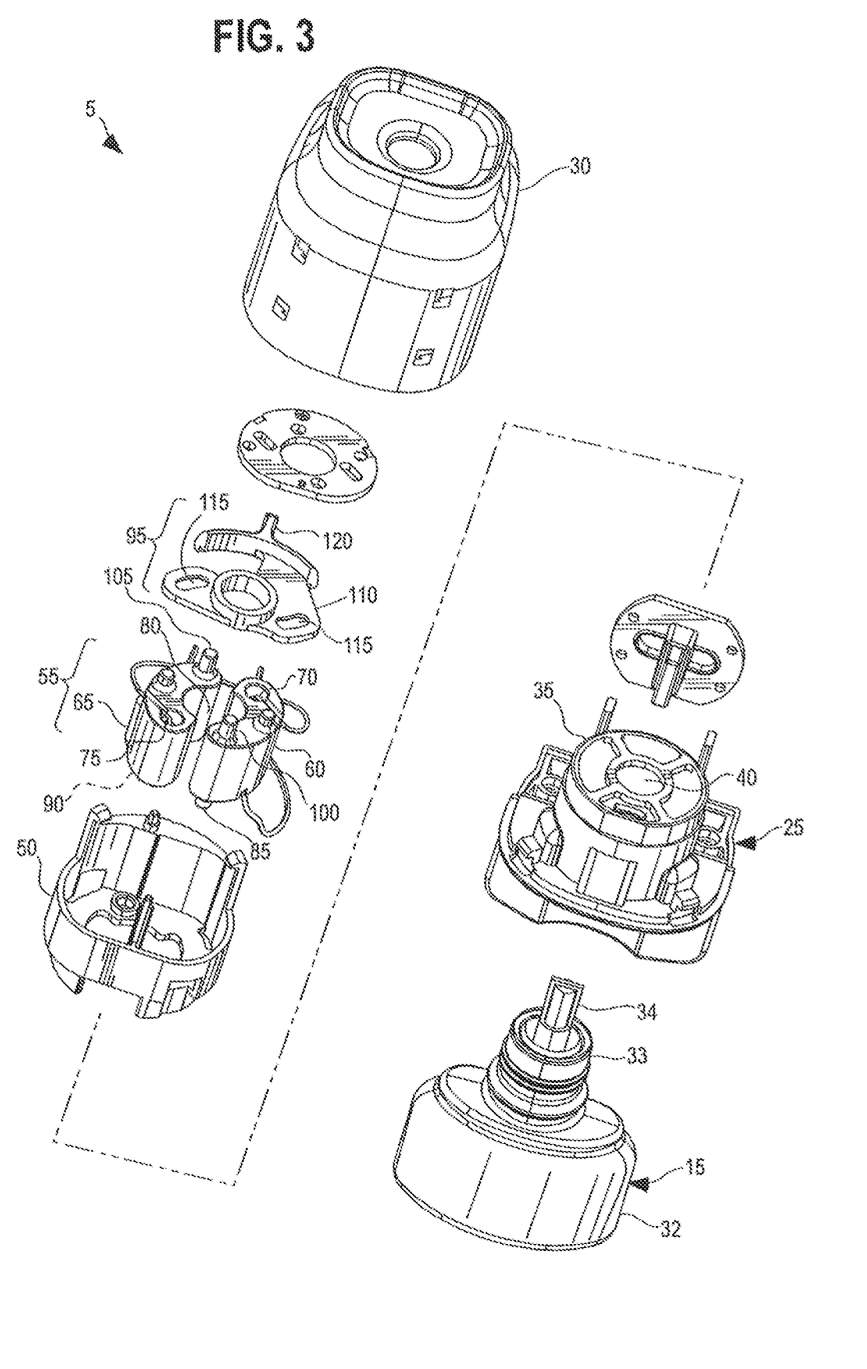
FIG. 3 is an exploded perspective view of the device of FIGS. 1 and 2.
Figure 4:
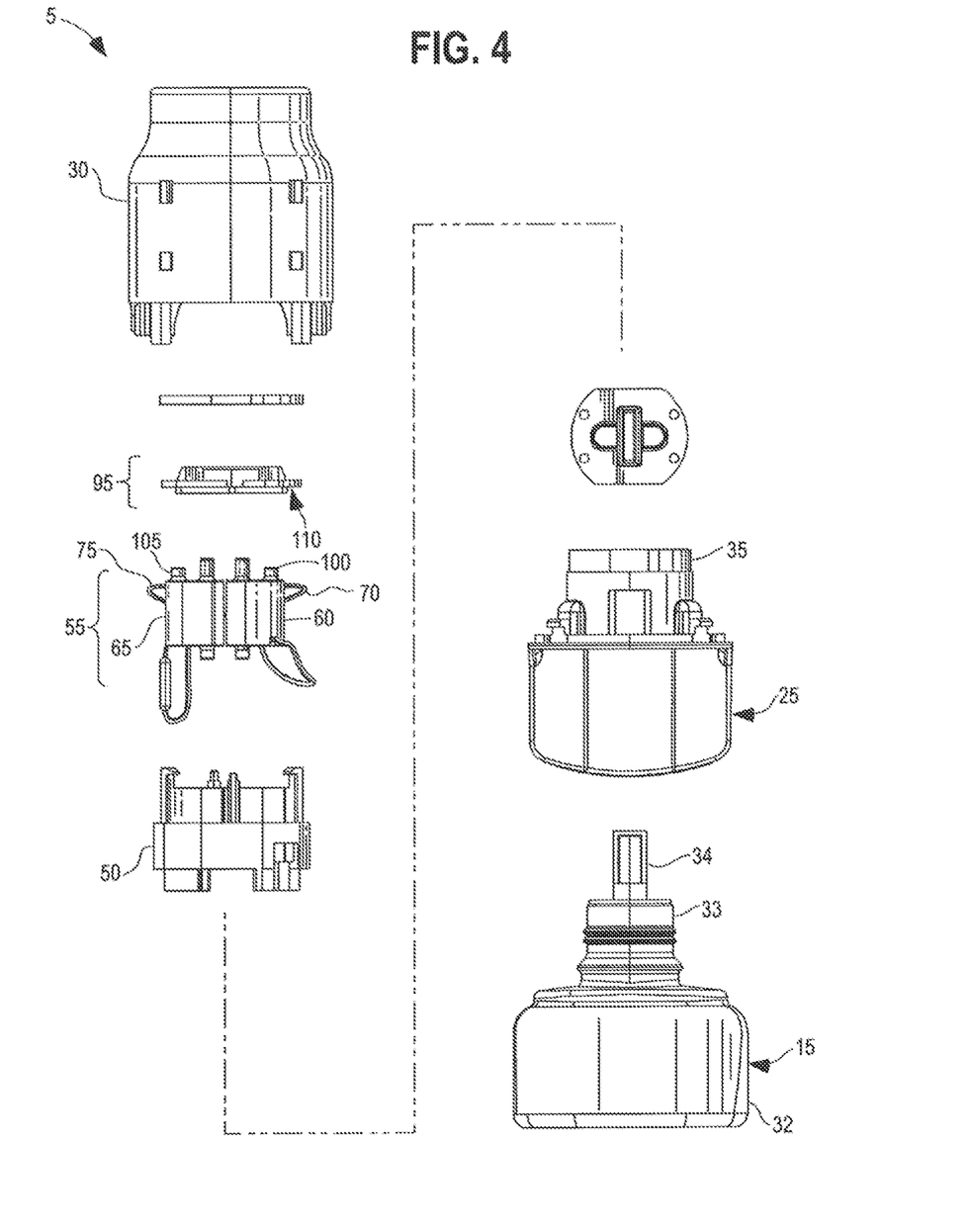
FIG. 4 is an exploded front view of the device of FIGS. 1-3.

The lower housing 25 includes a container receptacle 35 that is arranged to receive and releaseably secure the engagement section 33. The storage section 32 of the bottle 15 holds a compound to be volatilized. In the illustrated embodiment, the container receptacle 35 is a circular component with a container receptacle aperture 40 extending through the container receptacle 35. The container receptacle 35 may be other shapes and sizes as long as the container receptacle 35 is able to selectively engage with the engagement section 33 of the bottle 15. Referring to FIGS. 3 and 4, the container receptacle aperture 40 is shaped and sized so that the wick 34 may pass through the receptacle 35 and enter the interior of the lower housing 25. Within the interior of the lower housing 25, a heater cup 50 is mounted to the lower housing 25. In alternative embodiments, the heater cup 50 is mounted and supported by the container receptacle 35. The heater cup 50 serves as a base for and supports a heating mechanism 55 of the device.

The heating mechanism 55 includes first 60 and second 65 heating elements. In the illustrated embodiments, the first heating element 60 and the second heating element 65 are generally C-shaped structures as will be described in more detail hereinafter. In one embodiment, the heating elements 60, 65 are ceramic elements. However, it is contemplated within the scope of the present disclosure that any suitable material or alloy that is capable of providing suitable thermal conductivity could be used. Examples of such materials include zinc, aluminum, plated nickel, nichrome (80% nickel, 20% chromium), PTC (Positive Temperature Coefficient) rubber made of PDMS infused with carbon particles, and kanthal alloy (iron, chromium, and aluminum).

Each of the heating elements 60, 65 has a heating resistor 70, 75 embedded within the heating elements 60, 65, respectively. The heating resistors 70, 75 receive electrical current from a source that may be in form of a two or three prong electrical plug or a battery pack. In some embodiments, the heating resistors 70, 75 are oriented vertically within the heating elements 60, 65, or, relative to other components of the device, having their longer axis oriented parallel to the longer axes of the wick 34 and first and second heating elements 60, 65. This vertical arrangement advantageously aligns the length of the heating resistors 70, 75 with the length of the wick 34. This arrangement, in turn, creates heat adjacent to and along the entire height or length of the wick 34, which provides more efficient heat transfer. However, the present disclosure also contemplates a horizontal orientation of the heating resistors 70, 75—perpendicular to the heating elements 60, 65 and the wick 34. While such a horizontal arrangement provides for less efficient thermal transfer, the advantages of the present disclosure with respect to adjustable heating are retained.

While various shapes for the heating elements 60, 65 are contemplated within the present disclosure, FIGS. 2-5B depict the heating elements 60, 65 in a semi-circular cross-sectional shape (i.e., C-shaped). When combined, the two heating elements 60, 65 form a generally cylindrical shape having a vertical split parallel to the cylinder's longitudinal axis thereby forming a split cylinder surrounding the wick 34. Notably, this arrangement also creates a heating chamber or aperture 80 through the approximate center of the heating elements 60, 65. The wick 34, passing through the lower housing 25, container receptacle 35, and the heater cup 50, extends into a heating chamber or aperture 80 such that it is suitably positioned within the heating element aperture 80 adjacent to the heating elements 60, 65. The two heating elements 60, 65 therefore form a split cylinder surrounding the wick 34.

Figure 5A:
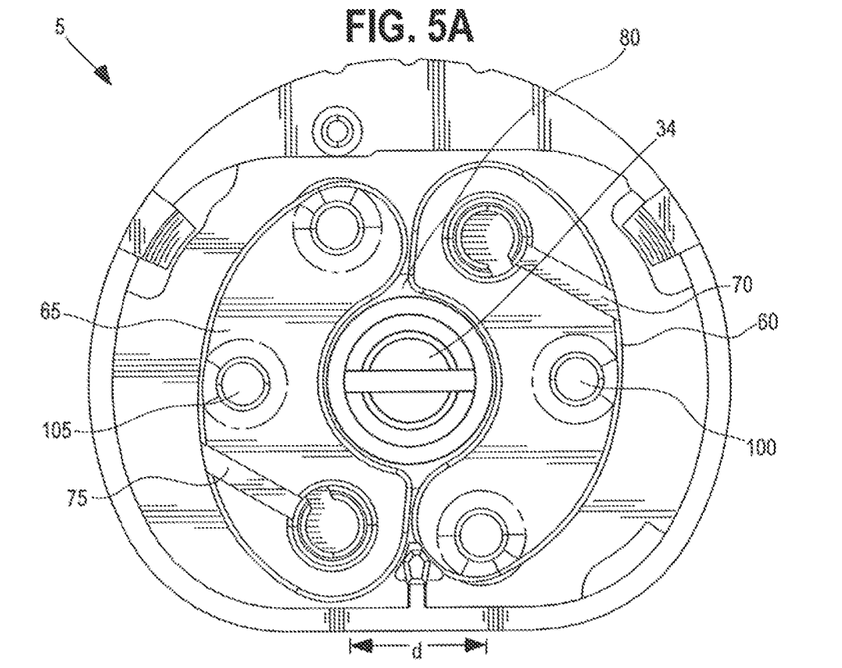
FIG. 5A is a schematic diagram of the heating elements of an embodiment when the heating elements are positioned closer to one another.
Figure 5B:
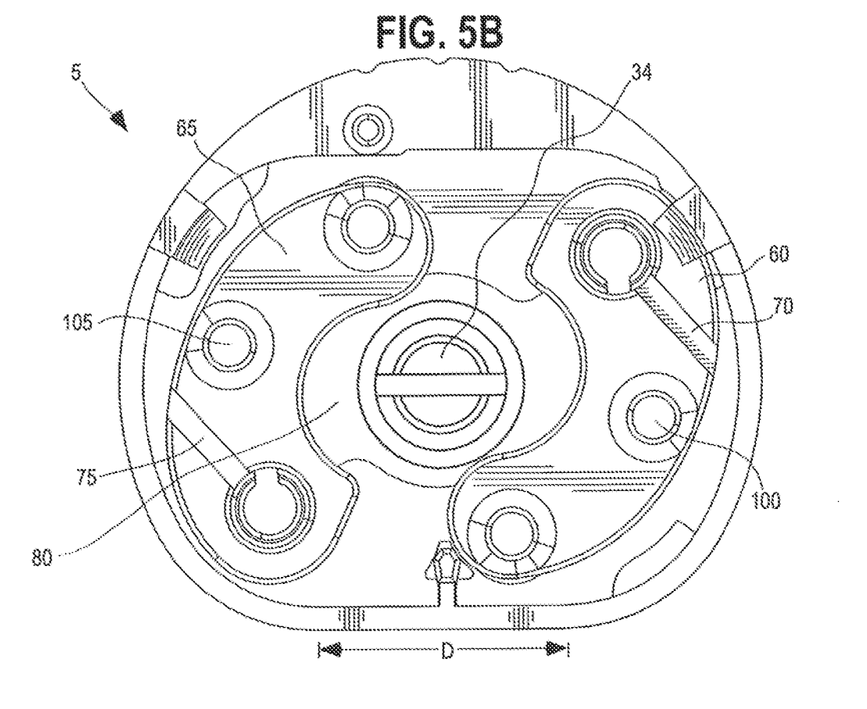
FIG. 5B is a schematic diagram of the heating elements of an embodiment when the heating elements are positioned farther from one another.

As illustrated in FIGS. 5A and 5B, the heating element aperture 80 is adjustable in the following manner. As noted previously, the heating elements 60, 65 are arranged in such a manner as to leave the open space of the heating element aperture 80 between the two heating elements 60, 65. The amount of heat delivered by the heating elements 60, 65 to the space represented by the heating element aperture 80 is proportional to a distance between the first 60 and second 65 heating elements. The heating resistors, 70, 75, being a fixed size and receiving a relatively steady flow of electricity, produce a generally steady amount of heat to the heating elements 60, 65. Therefore, the distance between the heating elements 60, 65 impacts the amount of heat delivered to the aperture 80 and, consequently, the wick 34. The closer that the two heating elements 60, 65 are to one another, the more heat that is created within the heating chamber or aperture 80. Conversely, when the two heating elements 60, 65 are farther from one another, less heat is created. Therefore, by adjusting the position of the heating elements 60, 65 relative to one another, a user may selectively adjust the amount of heat to which the wick 34 is exposed.

The amount of heat delivered to the wick 34 directly affects, and is generally proportional to, the burn rate of the wick or, more particularly, how much fuel, i.e., the compound in the bottle 15, is volatized to the atmosphere. The burn rate of the wick 34 translates—in the specific example of a fragrance—to the strength of the resulting scent that is perceptible to the user and others in the area. This rate of volatilization also relates directly to the rate at which the compound is drawn into the wick and, as a result, how quickly the container is emptied and must be replaced.

While the foregoing example referred specifically to a fragrance as the compound being volatilized, it is expressly contemplated within the present disclosure, and should be understood to be encompassed by the disclosure, that any substance that may be volatilized by application of heat could be used with a similar result.

FIGS. 5A and 5B illustrate one manner in which the size of the heating element aperture 80 may be adjusted by movement enabling structures associated with the heating elements 60, 65. For example, in one embodiment, the first heating element 60 is provided with a first lower pivot pin 85, which may be a first movement enabling structure. The first lower pivot pin 85 is a protrusion connected to and extending from the lower side of the first heating element 65. The first lower pivot pin 85 is preferably located at one end of the first heating element 60, and is rotatably mounted within a first mating aperture (not shown) in the upper surface of the heater cup 50. The first lower pivot pin 85 and the first mating aperture are arranged such that the first lower pivot pin 85 is able to rotate freely, without significant lateral movement, within the first mating aperture. In another arrangement encompassed within the present disclosure, the first lower pivot pin 85 may instead be formed as part of the heater cup 50 or an intervening component located between the heater cup 50 and the first heating element 60, and the first mating aperture may be formed in the lower surface of the first heating element 60.

Similarly, the second heating element 65 is provided with a second lower pivot pin 90, which may be a second movement enabling structure. The second lower pivot pin 90 is also a protrusion connected to and extends from the lower side of the second heating element 65. The second lower pivot pin 90 is preferably located at one end of the second heating element 65, and is rotatably mounted within a second mating aperture (not shown) in the upper surface of the heater cup 50. The second lower pivot pin 90 and the second mating aperture are arranged such that the second lower pivot pin 90 is able to rotate freely, without significant lateral movement, within the second mating aperture. In another arrangement encompassed within the present disclosure, the second lower pivot pin 90 may instead be formed as part of the heater cup 50 or an intervening component located between the heater cup 50 and the second heating element 65, and the second mating aperture may be formed in the lower surface of the second heating element 65.

The first 85 and second 90 lower pivot pins may be arranged either as separate elements that are press fit, welded, glued or otherwise secured within mounting holes in the appropriate element or integrally formed as part of the appropriate element.

The arrangement of the lower pivot pins 85, 90 with the heating elements 60, 65 allows the opposite ends of the heating elements 60, 65 to pivot inwardly or outwardly relative to the adjustable heating element aperture 80. Advantageously, the lower pivot pins 85, 90 may be associated with the same end of the respective first 60 and second 65 heating elements. Such an arrangement results in pivot points for the respective heating elements 60, 65, and the opposite, free ends of the heating elements 60, 65, having a relatively diagonal relationship to one another. This positional relationship allows the opposite ends of the heating elements 60, 65 to pivot away or toward each other, thereby increasing or decreasing the space between the heating elements 60, 65 and the heating element aperture 80. This feature is illustrated schematically in FIGS. 5A and 5B. FIG. 5A shows the heating elements 60, 65 in a position with the heating elements 60, 65 positioned relatively closer to one another, separated by a distance d. FIG. 5B illustrates the heating elements 60, 65 in a position after they have been pivoted away from each other, now separated by a distance D, with distance D being greater than distance d. In another embodiment, the device 5 may have various settings that correspond to the distance between the heating elements 60, 65. For example, the device 5 may have a high, medium, and low setting where the distance d correspondences to the high setting and the distance D corresponds to the low setting.

A user adjustment mechanism 95 that facilitates movement of the first 60 and second 65 heating elements is also provided. Each of the first 60 and second 65 heating elements is provided with an upper pivot pin 100, 105. In the illustrated device, the upper pivot pins 100, 105 are positioned at and extend from approximately from midpoint of the first 60 and second 65 heating elements, respectively. As illustrated in FIGS. 3 and 4, a pivot pin capture piece 110 having two pivot pin slots 115 and an adjustment lever 120 is provided to capture and engage the upper pivot pins 100, 105 with the slots 115. The pivot pin capture piece 110 and slots 115 help define a range of motion of the heating elements 60, 65 and direct the motion of the heating elements 60, 65.

More particularly, when adjustment lever 120 is rotated relative to a center of rotation of the pivot pin capture piece 110, the pivot pin slots 115 by their engagement with the upper pivot pins 100, 105 move the heating elements 60, 65 and cause them to pivot about the lower pivot pins 85, 90. Further, the orientation of the pivot pin slots 115, direct the free ends of the heating elements 60, 65 to move either away or toward one another depending upon the direction in which the adjustment lever 120 is moved. When the adjustment lever 120 is moved in a first direction, the pivot pin capture piece 110 and pivot pin slots 115 move the free ends of the heating elements 60, 65 away from one another, thereby decreasing the amount of heat within the adjustable heating element aperture 80 and delivered to the wick 34 as described above and seen in FIG. 5B. When the adjustment lever 120 is moved in the opposite or second direction, the pivot pin capture piece 110 and pivot pin slots 115 move the free ends of the heating elements 60, 65 toward one another, thereby increasing the amount of heat within the adjustable heating element aperture 80 and delivered to the wick 34 as described above and seen in FIG. 5A.

In the illustrated embodiment, the first 70 and second 75 heating resistors are positioned within the heating elements 60, 65 near the free ends thereof. Such an arrangement results in a greater degree of movement of the resistors 70, 75 relative to one another when the heating elements 60, 65 are moved relative to one another. This, in turn, may increase the available variability of heat delivered to the heating element aperture 80 and the wick 34 since the location of the resistors 70, 75 may represent the warmest portions of the heating elements 60, 65. However, it is contemplated within the scope of the present disclosure that the first 70 and second 75 heating resistors may be positioned elsewhere within the heating elements 60, 65 while still providing similar benefits of adjustable heating.

The upper housing 30 is advantageously arranged to allow user access to the adjustment lever 120 while also covering the heating elements 60, 65 to isolate the heating elements 60, 65 from the user, as shown in FIG. 1. This may be by means of a slot in the upper housing 30 through which the adjustment lever 120 extends or another arrangement.

It should be noted that while a pivoting arrangement for the heating elements 60, 65 is described herein, the present disclosure also encompasses other movement enabling structures that result in relative movement of two heating elements 60, 65 that cooperate to form an aperture 80 surrounding a wick 34 to result in adjustment of the amount of heat delivered to the wick. For example, the heating elements 60, 65 may be arranged in a sliding rather than pivoting relationship. Further, it is also contemplated that only one of the heating elements 60, 65 may be movable while the other is fixed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A device for adjustably heating a compound to disperse the compound by volatilization wherein the compound is delivered to a wick and exposed to a heat source, comprising:

a curvilinear first heating element, the first heating element including a first end and a second end;

a curvilinear second heating element, the second heating element including a first end and a second end;

wherein the first and second heating elements cooperate to form a heating chamber, and the wick is positioned within the heating chamber;

a first movement enabling structure associated with the first heating element;

a second movement enabling structure associated with the second heating element;

the first and second movement enabling structures being configured to allow movement of the first and second heating elements relative to one another;

an adjustment mechanism in mechanical communication with and cooperating with the first and second movement enabling structures, the first and second movement enabling structures in communication with and cooperating with the first and second heating elements, to produce selective relative movement of each of the first and second heating elements; and wherein movement of the adjustment mechanism in a first direction produces relative movement of each of the first and second heating elements toward one another and wherein movement of the adjustment mechanism in a second direction produces relative movement of each of the first and second heating elements away from one another, wherein in a first configuration, when the first and second heating elements are moved toward one another, the first end of the first heating element and the first end of the second heating element contact one another, and the second end of the first heating element and the second end of the second heating element contact one another to form the heating chamber such that the heating chamber completely surrounds a perimeter of the wick; and in a second configuration, when the first and second heating elements are separated from one another, the first and second heating elements cooperate to form the heating chamber such that the heating chamber does not completely surround the perimeter of the wick.

2. The device for adjustably heating a compound, as set forth in claim 1, wherein the first and second movement enabling structures are pins.

3. The device for adjustably heating a compound, as set forth in claim 1, wherein the adjustment mechanism further comprises an adjustment lever configured to move the adjustment mechanism in the first and second directions.

4. The device for adjustably heating a compound, as set forth in claim 1, wherein the first and second heating elements are configured to form a split cylinder surrounding the wick.

5. The device for adjustably heating a compound, as set forth in claim 1, further including a housing containing at least the first and second heating elements and wherein the user adjustment mechanism includes an adjustment lever that extends at least partially through the housing.

6. The device for adjustably heating a compound, as set forth in claim 1, wherein the first heating element includes a first resistor and the second heating element includes a second resistor and wherein the first and second resistors are configured parallel to a long axis of the first and second heating elements and the wick.

7. A method for adjustably heating a compound to disperse the compound by volatilization wherein the compound is delivered to a wick and exposed to a heat source, comprising the steps of:
providing a heat source including:
a curvilinear first heating element, the first heating element including a first end and a second end;
a curvilinear second heating element, the second heating element including a first end and a second end;
wherein the first and second heating elements cooperate to form a heating chamber within which the wick is positioned;
a first movement enabling structure associated with the first heating element;
a second movement enabling structure associated with the second heating element;
the first and second movement enabling structures being configured to allow movement of the first and second heating elements relative to one another;
an adjustment mechanism in mechanical communication with and cooperating with the first and second movement enabling structures, and the first and second movement enabling structures in communication with and cooperating with the first and second heating elements, to produce selective relative movement of the first and second heating elements; and
wherein movement of the adjustment mechanism in a first direction produces relative movement of each of the first and second heating elements toward one another and wherein movement of the adjustment mechanism in a second direction produces relative movement of each of the first and second heating elements away from one another;
positioning the wick within the heating chamber; and
adjusting an amount of heat within the heating chamber by moving the adjustment mechanism in at least one of the first direction and second direction;
wherein movement of the adjustment mechanism in the first direction causes the first end of the first heating element and the first end of the second heating element to contact one another, and the second end of the first heating element and the second end of the second heating element to contact one another to form the heating chamber such that the heating chamber completely surrounds a perimeter of the wick; and
wherein movement of the adjustment mechanism in the second direction causes the heating chamber to open such that it does not completely surround the perimeter of the wick.

8. The method for adjustably heating a compound, as set forth in claim 7, wherein the first and second movement enabling structures are pins.

9. The method for adjustably heating a compound, as set forth in claim 7, wherein the adjustment mechanism further comprises an adjustment lever configured to allow a user to move the adjustment mechanism in the first and second directions.

10. The method for adjustably heating a compound, as set forth in claim 7, wherein the first and second heating elements are configured to form a split cylinder surrounding the wick.

11. The method for adjustably heating a compound, as set forth in claim 7, wherein the device includes a housing containing at least the first and second heating elements and wherein the user adjustment mechanism includes an adjustment lever that extends at least partially through the housing.

12. The method for adjustably heating a compound, as set forth in claim 7, wherein the first heating element includes a first resistor and the second heating element includes a second resistor and wherein the first and second resistors are configured parallel to a long axis of the first and second heating elements and the wick.

13. A device for volatizing compounds comprising:
a curvilinear first heating element, the first heating element including a first end and a second end and a curvilinear second heating element, the second heating element including a first end and a second end; the first heating element and second heating element forming a heating element aperture of variable diameter;
a wick extending at least partially into the heating element aperture; and
an adjustment mechanism engaging the first heating element and second heating element, the adjustment mechanism selectively adjusting the distance of each of the first heating element and the second heating element from the wick;
wherein, in a first configuration, the first end of the first heating element and the first end of the second heating element contact one another, and the second end of the first heating element and the second end of the second heating element contact one another to heating elements form a heating element aperture surrounding a perimeter of the wick and having a first diameter; and
in a second configuration, the first and second heating elements form a heating element aperture that does not completely surround the perimeter of the wick and having a second diameter;
wherein the first diameter is smaller than the second diameter.

14. The device of claim 13 wherein the device further includes a first movement enabling structure associated with the first heating element; and
a second movement enabling structure associated with the second heating element.

15. The device of claim 14 wherein the adjustment mechanism mechanically engages the first movement enabling structure and the second movement enabling structure to selectively increase or decrease the width of the heating element aperture.

16. The device of claim 15 wherein the first and second movement enabling structures are pins.

17. The device of claim 13 wherein the first and second heating elements are configured to form a split cylinder surrounding the wick.

18. The device of claim 13 wherein the adjustment mechanism further comprises an adjustment lever configured to allow a user to move the adjustment mechanism in the first and second directions.

19. The device of claim 13 wherein a housing contains at least the first and second heating elements and wherein the user adjustment mechanism includes an adjustment lever that extends at least partially through the housing.

20. The device of claim 13 wherein the first heating element includes a first resistor and the second heating element includes a second resistor and wherein the first and second resistors are configured parallel to a long axis of the first and second heating elements and the wick.

\* \* \* \* \*